(12) United States Patent
Vilinsky

(10) Patent No.: US 9,295,618 B2
(45) Date of Patent: Mar. 29, 2016

(54) PERSONAL CARE PRODUCTS CONTAINING RAINWATER

(71) Applicant: P.V. Creations, Fair-Lawn, NJ (US)

(72) Inventor: Pnina Vilinsky, Fair Lawn, NJ (US)

(73) Assignee: PV CREATIONS LLC, Fair Lawn, NJ (US)

( * ) Notice: Subject to any disclaimer, the term of this patent is extended or adjusted under 35 U.S.C. 154(b) by 0 days.

(21) Appl. No.: 14/015,188

(22) Filed: Aug. 30, 2013

(65) Prior Publication Data

US 2013/0344164 A1 Dec. 26, 2013

Related U.S. Application Data

(62) Division of application No. 13/059,578, filed as application No. PCT/US2009/054784 on Aug. 24, 2009.

(60) Provisional application No. 61/090,969, filed on Aug. 22, 2008.

(51) Int. Cl.
| | |
|---|---|
| *A61K 36/72* | (2006.01) |
| *A61K 36/898* | (2006.01) |
| *A61K 36/00* | (2006.01) |
| *A61K 33/00* | (2006.01) |
| *A61K 8/19* | (2006.01) |
| *A61K 8/73* | (2006.01) |
| *A61K 8/97* | (2006.01) |
| *A61Q 19/00* | (2006.01) |

(52) U.S. Cl.
CPC . *A61K 8/19* (2013.01); *A61K 8/732* (2013.01); *A61K 8/97* (2013.01); *A61Q 19/00* (2013.01)

(58) Field of Classification Search
CPC ..... A61K 36/185; A61K 36/82; A61K 36/28; A61K 45/06; A61K 8/97
See application file for complete search history.

(56) References Cited

U.S. PATENT DOCUMENTS

| | | | |
|---|---|---|---|
| 5,024,546 A * | 6/1991 | Guzman et al. | 401/16 |
| 2006/0234886 A1 | 10/2006 | Massaro et al. | |
| 2007/0122492 A1* | 5/2007 | Behr et al. | 424/725 |
| 2007/0134193 A1* | 6/2007 | Pauly et al. | 424/74 |
| 2007/0196296 A1 | 8/2007 | Osborne et al. | |
| 2007/0224229 A1* | 9/2007 | Gibbons et al. | 424/401 |
| 2009/0232758 A1* | 9/2009 | Archambault et al. | 424/63 |

OTHER PUBLICATIONS

International Search Report from International Application No. PCT/US09/054784, Mailed on Dec. 17, 2009.
Office Action for U.S. Appl. No. 13/059,578, dated Jun. 13, 2012.
Final Office Action for U.S. Appl. No. 13/059,578, dated Mar. 1, 2013.
Oregon Rain Source Test, Edge Analytical Laboratories, 2007, available at http://www.oregon-rain.com/eolabottling/ Oregon_Rain_Source_Test_2007.pdf.

* cited by examiner

*Primary Examiner* — Chris R Tate
*Assistant Examiner* — Russell Fiebig
(74) *Attorney, Agent, or Firm* — Pearl Cohen Zedek Latzer Baratz LLP

(57) ABSTRACT

This invention relates generally to formulations and methods for improving level of moisture absorption and retention by the skin and for improving the appearance, feel, or comfort of the skin, wherein the formulations comprise pure rainwater. In another embodiment of the invention, the formulations comprise a combination of natural extracts. The present invention is a formulation made substantially without the use of synthetic chemicals and petroleum by-products, wherein the formulation is used for personal care. More specifically, the present invention is a skin care product formulation wherein 90% or more of the ingredients are natural products.

9 Claims, 1 Drawing Sheet

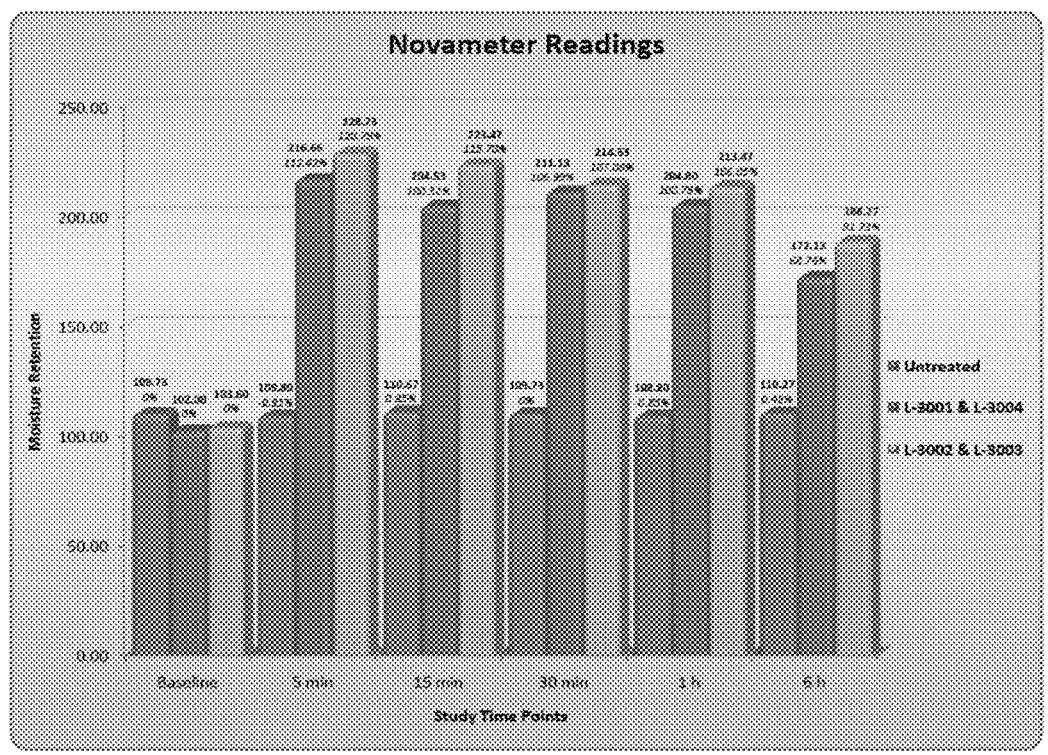

PERSONAL CARE PRODUCTS CONTAINING RAINWATER

CROSS REFERENCE TO RELATED APPLICATIONS

This application is a divisional of U.S. patent application Ser. No. 13/059,578, filed Feb. 17, 2011 as a national phase under 35 U.S.C. §371 of PCT International Patent Application No. PCT/US2009/054784, filed Aug. 24, 2009, which claimed priority from U.S. Provisional patent application No. 61/090,969, filed Aug. 22, 2008, each of which is incorporated herein by reference in its entirety entireties.

FIELD OF THE INVENTION

This invention relates generally to formulations and methods for improving and retaining the moisture level in the skin and for improving the appearance, feel, or comfort of the skin by increasing the moisture level in the skin. More specifically, the invention relates to formulations comprising pure rainwater and/or a combination of natural extracts and the application of such formulations to the skin for cosmetic reasons.

BACKGROUND OF THE INVENTION

Many substances are applied topically to the skin or mucous membranes of humans or animals (hereinafter "skin") in order to alter the subject's appearance, to protect the subject from the environment, or to produce a biological change in the skin or other tissue for therapeutic, preventive or cosmetic purposes. These substances may generically be termed "topical products" and include such topically applied substances as cosmetics, topical over-the-counter or prescription medications, soaps and cleansers.

Topical products occur in a variety of forms, including solids, liquids, suspensions, semisolids (such as creams, gels, lotions, pastes or "sticks"), powders or finely dispersed liquids such as sprays or mists. Examples of topical products commonly classified as "cosmetics" include skin care products such as moisturizing creams and lotions, and "treatment cosmetics" such as exfoliants and/or skin cell renewal agents; fragrances such as perfumes and colognes, and deodorants; shaving-related products such as creams, "bracers" and aftershaves; depilatories and other hair removal products; skin cleansers, toners and astringents; pre-moistened wipes and washcloths; tanning lotions and sunscreens; bath products such as oils; eye care products such as eye lotions and makeup removers; foot care products such as powders and sprays; skin colorant and make-up products such as foundations, blushes, rouges, eye shadows and liners, lip colors and mascaras; lip balms and sticks; hair care and treatment products such as shampoos, conditioners, colorants, dyes, bleaches, straighteners, and permanent wave products; baby products such as baby lotions, oils, shampoos, powders and wet wipes; feminine hygiene products such as deodorants and douches; skin or facial peels applied by dermatologists or cosmeticians; and others. Examples of topical products commonly classified as "topical drugs" are many and varied, and include over-the-counter and/or prescription products such as antiperspirants, insect repellents, sunscreens and sunburn treatments, anti-acne agents, antibiotics, therapeutic retinoids, anti-dandruff agents, external analgesics such as capsaicin products, topical contraceptives, topical drug delivery systems, suppositories and enemas, hemorrhoid treatments, vaginal treatments, lozenges, and many other products with therapeutic or other effects. Other topical products include hand, facial and body soaps and detergents and other forms of skin cleansers, as well as household detergents and many other household products such as solvents, propellants, polishes, lubricants, adhesives, waxes and others which are either applied topically or are topically exposed to the body during normal use.

Many ingredients used in topical products are known irritants or are potentially irritating, especially to people with "sensitive skin". These irritating ingredients include fragrances, preservatives, solvents, propellants and many other ingredients that might otherwise be considered inert components of the products. Additionally, many active ingredients, including chemicals that may also be classified as drugs, produce irritation when applied to the skin. Where more than one chemical irritant is present, their irritating effects may be additive. Furthermore, chemical ingredients may react with one another, or in the environment of the skin, to form new chemicals which are irritating.

Furthermore, as people age, their skin loses elasticity and is unable to retain moisture as well. Thus, many people experience dry skin as they age and require moisturizers that penetrate more deeply so that the moisture is retained for a longer period of time. Adding moisture to the skin provides comfort and relief from flaking or itching and reduces the appearance of wrinkles. It is important to formulate these products from environmentally sustainable materials, so that natural resources are not depleted.

There is a need for personal care products formulated almost without the use of chemicals and petroleum by-products. The purpose of creating such formulations/products is to allow consumers/users of personal care products to enjoy safer products than the ones that exist in today's market, while also providing improved performance in moisturizing the skin and being more environmentally sustainable. Particularly, it would be useful to have personal care products wherein 90% or more of the ingredients are natural products. It is known that the use of natural products result in lower health risks than the use of chemicals or petroleum by-products that are commonly used in personal care products today, e.g., avoiding the use of parabens as preservatives and using a natural preservative system, using a natural fragrance and avoiding the use of a synthetic fragrance (see http://www.cosmeticsdatabase.com/wordsearch.php?query=paraben regarding the dangers of parabens).

Although it is recognized that personal care products need to use purified water for consumer safety purposes (see http://www.cosmeticsinfo.org/ingredient_details.php?ingredient_id=1566), most manufacturers and vendors of personal care and cosmetic products do not go beyond the minimum government requirements set forth for water quality. The reason for monitoring water quality in personal care products has been for the purpose of consumer safety (see http://www.ewg.org/health/report/bottledwater-scorecard and http://www.ewg.org/reports/bottledwater and http://www.cosmeticsdatabase.com/browse.php?category=nourishing), but the focus has not been on improving the performance of personal care products by using purified water.

There is also a need for a product or skincare regimen that can increase the level of moisture in the skin to improve the appearance and feel of the skin and relieve dryness, flaking and itchiness, where the product is made from natural, non-irritating ingredients that are environmentally sustainable.

SUMMARY OF THE INVENTION

This invention relates generally to formulations and methods for improving the appearance, feel, or comfort of the skin, wherein the formulations comprise pure rainwater. The present invention relates to personal care products formulated using pure rainwater that has not touched the earth, thus having less than trace amounts of minerals and other elements. In another embodiment of the invention, the formulations comprise a combination of rare natural extracts.

The present invention is a formulation made substantially without the use of synthetic chemicals and petroleum by-products, wherein the formulation is used for personal care. More specifically, the present invention is a skin care product formulation wherein 90% or more of the ingredients are natural products. It has been shown that the natural products contained in the disclosed formulations as embodiments of the within invention result in lower health risks than chemicals or petroleum by-products commonly used in personal care products today. The formulations of the present invention avoid the use of parabens as preservatives, instead using a natural preservative system. The formulations of the present invention also use a natural fragrance and avoid the use of synthetic fragrance, which is very common.

BRIEF DESCRIPTION OF THE DRAWINGS

For a more complete understanding of the present invention and the advantages thereof, reference should be made to the following Detailed Description taken in conjunction with the accompanying drawings in which:

FIG. 1 is a graphical representation of NOVA dermal phase meter results from a moisturization study comparing formulations of the present invention.

DETAILED DESCRIPTION OF THE INVENTION

The present invention is formulations comprising pure rainwater and methods of using such formulations for improving the appearance, feel, or comfort of the skin, wherein the formulations comprise pure rainwater. Water is one of the most precious commodities in the world. The rainwater used in the present invention is much more pure than water currently used in personal care products because it is pure rainwater that has not touched the earth and has been further purified to remove minerals and contaminants. With water being in short supply in many parts of the world, another advantage to using rainwater is that it is an environmentally sustainable resource. Using rainwater also minimizes anthropogenic interference while using natural resources.

In another embodiment of the invention, the formulations comprise a combination of natural extracts. Specifically, the formulations comprise a combination of six extracts: *anastatica hierochuntica* (resurrection plant) extract, *hippophae rhamnoides* (sea buckthorn) extract, *passiflora incarnata* fruit (passionfruit) extract, *orchis mascula* (orchid) flower extract, *punica granatum* (pomegranate) extract, and *portulaca oleracea* extract.

The present invention is a formulation made substantially without the use of synthetic chemicals and petroleum by-products, wherein the formulation is used for personal care. One embodiment of the present invention is a skin care product formulation wherein 90% or more of the ingredients are natural products. It has been shown that the natural products contained in the disclosed formulations as embodiments of the present invention result in lower health risks than chemicals or petroleum by-products commonly used in personal care products today. The formulations of the present invention avoid the use of parabens as preservatives, instead using a natural preservative system. The formulations of the present invention also use a natural fragrance and avoid the use of synthetic fragrance, which is very common.

More particularly, this invention relates to personal care products, particularly skincare products that contain pure rainwater as the main ingredient. In this regard, the skincare product formulations of this invention utilize pure rainwater, and more specifically, rainwater that is free from even trace levels of minerals, elements and chemicals ordinarily found in most water supplies, including natural spring waters. Rainwater that is utilized in the formulations of this invention is collected by a method that avoids contact with the ground, so that the rainwater does not pick up trace elements and minerals from the soil. Once collected, the rainwater is filtered through a microporous filter, such as a 0.35 micron filter, and also through an activated carbon filter. Optionally, the rainwater may be ozonated as a further level of purification. Rainwater of this type may be obtained from, for example, Oregon Rain, Inc., of Salem, Oreg. Typical test results for such rainwater indicates that it has a sodium level at a minimum detection limit (MDL) of 0.03 mg/L and a practical quantitation limit (PQL) of 0.50 mg/L; hardness level of 0.35 mg/L MDL and 10 mg/L PQL; calcium level of 0.017 mg/L MDL and 1 mg/L PQL; and magnesium level of 0.003 mg/L MDL and 1 mg/L PQL (see http://oregon-rain.com/Oregon_Rain_Source_Test_2007.pdf). Embodiments of the present invention comprise pure rainwater having similar properties and at least lower levels than currently acceptable for drinking water.

The Pacific Ocean rainwater used in the embodiments of the invention described herein was chosen because of its particularly superior location. The Northern Pacific Coastline, with its exceptionally clean air and its ocean winds, which brought the moisture-rich clouds from their original place of creation, provides a soft, fresh, clean rain. This clean rainwater is collected without touching the ground, preventing it from having added dissolved minerals and organic substances, contaminants or toxins that may exist in the soil. The rainwater is soft and low in dissolved minerals, allowing it to penetrate more efficiently into the skin, unlike heavy mineralized water, making it a more efficient carrier for ingredients to the skin.

Clinical results show that formulations that contain pure rainwater versus same formulations using purified water have better results in adding moisture to the skin and in helping the skin retain that moisture when applied topically. The personal care products using rainwater of this invention may be any of the following: facial lotions; facial creams; facial serums; eye creams; facial masks (beauty masks); facial mists; facial toners; facial cleansers; facial scrubs/exfoliates; facial wipes; neck creams; body lotions; body creams; body mists; body serums; body scrubs; hand creams; foot creams; shaving creams; aftershave lotions; hair masks; hair treatment products; hair shampoos; hair conditioners; hair serums; hair rinses; body splashes; natural fragrances; hand masks; foot masks; body soaks; liquids for the bath; body soaps; facial soaps; nutraceutical drinks; nutraceutical products; nutraceutical gels; natural deodorants; natural air fresheners; natural laundry softener liquid; natural laundry detergents; baby soaps; baby lotions; baby wipes; baby shampoos; baby conditioners; baby creams; baby laundry natural detergents; baby laundry natural softeners; mouthwash; children's mouthwash, and the like.

EXAMPLE 1

Deep Moisturizing Lotion

An example of a personal care product of the present invention is a deep moisturizing lotion. Moisturizing lotions comprise mostly water, and also contain a variety of ingredients and ingredient combinations. One embodiment of the present invention is a moisturizing lotion formulation comprising 5-99% by weight of pure rainwater and 0.1-5% by weight of each of the following: naturally-derived Glycerin, Dimethicone, Cetearyl Alcohol, Caprylic/Capric Triglyceride, *Butyrospermum Parkii* (Shea Butter), Candelilla/Jojoba/Rice Bran Polyglyceryl-3 Esters, Glyceryl Stearate, *Carthamus Tinctorius* (Safflower) Seed Oil, Cetearyl Glucoside, *Borago Officinalis* Seed Oil, *Oenothera Biennis* (Evening Primrose) Oil, *Anastatica Hierochuntica* Extract, *Hippophae Rhamnoides* Extract, *Passiflora Incarnata* Fruit Extract, *Orchis Mascula* Flower Extract, *Punica Granatum* Extract, Sodium Hyaluronate, Tocopheryl Acetate, Sodium Stearyl Lactylate, Sodium Coco-Glucoside Tartrate, Disodium Coco-Glucoside Tartrate, *Triticum Vulgare* (Wheat Germ) Oil, *Persea Gratissima* (Avocado) Oil, *Algae* Extract, *Zea Mays* (Corn) Starch, Hydrolyzed Corn Starch, Hydrolyzed Starch Octenylsuccinate, Cocamidopropyl Dimethylamine, Lauryl Laurate, Palmitoyl Tripeptide-5, *Portulaca Oleracea* Extract, and one or more natural preservatives and one or more natural aroma-imparting oils. An embodiment of a deep moisturizing lotion formulation of this invention is shown in Table 1. It will be appreciated by one of skill in the art that moisturizing lotions similar to this embodiment may be made by varying the amounts of the particular ingredients. The weight percentage of pure rainwater may be from 5 to 99%. The weight percentages of the other ingredients generally range from about 0.1000% to 5.000%. Glycerin, which is a humectant that helps retain moisture, can typically be synthetically-derived (e.g., from propylene alcohol) or naturally-derived from vegetables or plants. In the present invention, the glycerin contained in the formulations is all naturally-derived from vegetables or plants.

TABLE 1

Deep Moisturizing Lotion

Ingredient

Pure Pacific Ocean Rainwater (Aqua)
Glycerin (naturally-derived from vegetables or plants)
Dimethicone
Cetearyl Alcohol
Caprylic/Capric Triglyceride
*Butyrospermum Parkii* (Shea Butter)
Candelilla/Jojoba/Rice Bran Polyglyceryl-3 Esters
Glyceryl Stearate
*Carthamus Tinctorius* (Safflower) Seed Oil
Cetearyl Glucoside
*Borago Officinalis* Seed Oil
*Oenothera Biennis* (Evening Primrose) Oil
*Anastatica Hierochuntica* Extract
*Hippophae Rhamnoides* Extract
*Passiflora Incarnata* Fruit Extract
*Orchis Mascula* Flower Extract
*Punica Granatum* Extract
Sodium Hyaluronate
Tocopheryl Acetate
Sodium Stearyl Lactylate
Sodium Coco-Glucoside Tartrate
Disodium Coco-Glucoside Tartrate
*Triticum Vulgare* (Wheat Germ) Oil
*Persea Gratissima* (Avocado) Oil
Algae Extract
*Zea Mays* (Corn) Starch
Hydrolyzed Corn Starch
Hydrolyzed Starch Octenylsuccinate
Cocamidopropyl Dimethylamine
Lauryl Laurate
Palmitoyl Tripeptide-5
Butylene Glycol TABLE 1-continued Deep Moisturizing Lotion

*Portulaca Oleracea* Extract
*Lonicera Caprifolium* (Honeysuckle) Flower Extract
*Lonicera Japonica* (Honeysuckle) Flower Extract
Xanthan Gum
Hydroxyethyl Acrylate/Sodium Acryloyldimethyl Taurate Copolymer
Squalane
Polysorbate 60
Potassium Sorbate
Citric Acid
Geraniol
Amyl Cinnamal
Cinnamal
Citral
Citronellol
Limonene
Linalool
*Citrus Aurantium Dulcis* (Orange) Peel Oil
Aldehyde C-14 Natural
*Cinnamomum Zeylanicum* Leaf Oil
*Illicium Verum* (Anise) Fruit/Seed Oil
Benzyl Acetate Natural
*Cinnamomum Cassia* Oil
*Mentha Arvensis* Leaf Oil
*Pyrus Malus* (Apple) Oil
*Cymbopogon Nardus* (Citronella) Oil
*Cucumis Sativus* (Cucumber) Oil
*Prunus Amygdalus Dulcis* (Sweet Almond) Oil
*Pelargonium Graveolens* Extract
*Corylus Avellana* (Hazel) Seed Oil
*Cymbopogon Martini* Oil
*Cymbopogon Schoenanthus* Oil
*Listea Cubeba* Fruit Oil
*Cinnamomum Camphora* (Camphor) Bark Oil
*Citrus Medica Limonum* (Lemon) Peel Oil
*Mentha Citrata* Leaf Extract
*Pinus Palustris* Oil

EXAMPLE 2

Hydrating Water Mist

Another embodiment of the present invention is a hydrating water mist. Hydrating water mists comprise mostly water, and also contain a variety of ingredients and ingredient combinations. One embodiment of the present invention is a formulation comprising 5-99% by weight of pure rainwater and 0.1-5% by weight of each of the following: *Hamamelis Virginiana* (Witch Hazel) Water, Alcohol (denatured), Sodium Hyaluronate, naturally-derived Glycerin, *Anastatica Hierochuntica* (Resurrection Plant) Extract, *Hippophae Rhamnoides* (Sea Buckthorn) Extract, *Passiflora Incarnata* Fruit (Passion Fruit) Extract, *Orchis Mascula* (Orchid) Flower Extract, *Punica Granatum* (Pomegranate) Extract, *Portulaca Oleracea* Extract, Methyl Diisopropyl Propionamide, Ethyl Menthane Carboxamide, Menthyl Lactate, Lauryl Laurate, *Zea Mays* (Corn) Starch, Hydrolized Corn Starch, Hydrolyzed Corn Starch Octenylsuccinate, and one or more natural preservatives and one or more natural aroma-imparting oils. An embodiment of a hydrating water mist formulation of this invention is shown in Table 2. It will be appreciated by one of skill in the art that hydrating water mists similar to this embodiment may be made by varying the amounts of the particular ingredients. The weight percentage of water may be from 5 to 99%. The weight percentages of the other ingredients generally range from about 0.1000% to 5.000%.

TABLE 2

Hydrating Water Mist

Ingredients

Pure Pacific Ocean Rainwater (Aqua)
Polysorbate 20
*Hamamelis Virginiana* (Witch Hazel) Water
Alcohol, denatured
Sodium Hyaluronate
Glycerin (naturally-derived from vegetables or plants)
*Anastatica Hierochuntica* Extract
*Hippophae Rhamnoides* Extract
*Passiflora Incarnata* Fruit Extract
*Orchis Mascula* Flower Extract
*Punica Granatum* Extract
Butylene Glycol
*Portulaca Oleracea* Extract
Methyl Diisopropyl Propionamide
Ethyl Menthane Carboxamide
Menthyl Lactate
Lauryl Laurate
*Zea Mays* (Corn) Starch
Hydrolized Corn Starch
Hydrolyzed Corn Starch Octenylsuccinate
*Lonicera Caprifolium* (Honeysuckle) Flower Extract
*Lonicera Japonica* (Honeusuckle) Flower Extract
Potassium Sorbate
Citric Acid
Sodium Phytae
Citronellol
Limonene
Linalool
*Citrus Aurantium Dulcis* (Orange) Peel Oil
Aldehyde C-14 Natural
*Cinnamomum Zeylanicum* Leaf Oil
*Illicium Verum* (Anise) Fruit/Seed Oil
Benzyl Acetate Natural
*Cinnamomum Cassia* Oil
*Mentha Arvensis* Leaf Oil
*Pyrus Malus* (Apple) Oil
*Cymbopogon Nardus* (Citronella) Oil
*Cucumis Sativus* (Cumcumber) Oil
*Prunus Amygdalus Dulcis* (Sweet Almond) Oil
*Pelargonium Graveolens* Extract
*Corylus Avellana* (Hazel) Seed Oil
*Cymbopogon Martini* Oil
*Cymbopogon Schoenanthus* Oil
*Listea Cubeba* Fruit Oil
*Cinnamomum Camphora* (Camphor) Bark Oil
*Citrus Medica Limonum* (Lemon) Peel Oil
*Mentah Citrata* Leaf Extract
*Pinus Palustris* Oil

EXAMPLE 3

Deep Moisturizing Serum

Another example of a personal care product of this invention is a deep moisturizing serum. A deep moisturizing serum helps to seal the moisture into the skin. The serum comprises a combination of natural extracts and essential oils that helps to moisturize skin and ingredients to seal in moisture. An embodiment of a deep moisturizing serum formulation of the invention is shown in Table 3. The weight percentages of the essential oils and extracts (designated by an asterisk) generally range from about 0.1000% to 10.000%:

TABLE 3

Deep Moisturizing Serum

Ingredients:

Cyclopentasiloxane
Dimethicone Crosspolymer

TABLE 3-continued

Deep Moisturizing Serum

Tocopheryl Acetate
Lauryl PEG-9 Polydimethylsiloxyethyl Dimethicone
*Carthamus Tinctorius* (Safflower) Seed Oil*
*Rosa Rubiginosa* Seed Oil*
*Oenothera Biennis* (Evening Primrose) Oil*
Polyglyceryl-4 Isostearate
Palmitoyl Oligopeptide
Palmitoyl Tetrapeptide-7
Ascorbic Acid
PEG-12 Dimethicone Crosspolymer
*Borago Officinalis* Seed Oil*
*Anastatica Hierochuntica* Extract*
*Hippophae Rhamnoides* Extract*
*Passiflora Incarnata* Fruit Extract*
*Orchis Mascula* Flower Extract*
*Punica Granatum* Extract*
Butylene Glycol
*Portulaca Oleracea* Extract*
Amyl Cinnamal
Cinnamal
Citral
Citronellol
Coumarin
Geraniol
Limonene
Linalool
*Citrus Aurantium Dulcis* (Orange) Peel Oil
Aldehyde C-14 Natural
*Cinnamomum Zeylanicum* Leaf Oil
*Illicium Verum* (Anise) Fruit/Seed Oil
Benzyl Acetate Natural
*Cinnamomum Cassia* Oil
*Mentha Arvensis* Leaf Oil
*Pyrus Malus* (Apple) Oil
*Cymbopogon Nardus* (Citronella) Oil
*Cucumis Sativus* (Cucumber) Oil
*Prunus Amygdalus Dulcis* (Sweet Almond) Oil
*Pelargonium Graveolens* Extract
*Corylus Avellana* (Hazel) Seed Oil
*Cymbopogon Martini* Oil
*Cymbopogon Schoenanthus* Oil
*Listea Cubeba* Fruit Oil
*Cinnamomum Camphora* (Camphor) Bark Oil
*Citrus Medica Limonum* (Lemon) Peel Oil
*Mentha Citrata* Leaf Extract
*Pinus Palustris* Oil In another embodiment of the deep moisturizing serum, the formulation comprises 0.20% by weight to 5% of each of the following: *Anastatica Hierochuntica* Extract, *Hippophae Rhamnoides* Extract, *Passiflora Incarnata* Fruit Extract, *Orchis Mascula* Flower Extract, *Punica Granatum* Extract, and *Portulaca Oleracea* Extract.

EXAMPLE 4

Moisturization Study

A moisturization study conducted by AMA Laboratories, Inc. (New City, N.Y.) of the above moisturizing lotion and hydrating water mist formulations compared the use of rainwater in those formulations with the use of regular "purified water" in a single blind study. The studies measured the moisturization of the skin of a subject when both the hydrating mist and moisturizing lotion were applied consecutively. Five subjects were tested. In the study, samples L-3001 (hydrating water mist) and L-3004 (deep moisturizing lotion) were formulated using purified water. Samples L-3002 (hydrating water mist) and L-3003 (deep moisturizing lotion) are identical formulations to L-3001 (hydrating water mist) and L-3004 (deep moisturizing lotion), except that they were formulated using the pure rainwater of the present invention.

In this case, the pure rainwater is pure Pacific Ocean rainwater (Oregon Rain, Inc., Newberg, Oreg.). The NOVA dermal phase meter (Model DPM 9003, NOVA Technology Corporation, Gloucester, Mass.) is an instrument designed to measure skin moisture. The subjects of study were females between the ages of 39 to 52, exhibiting self-assessed dry skin and having the presence of fine lines and wrinkles in the upper facial and eye area regions. Subjects were required to abstain from using any wrinkle treatment and moisturizing products, including lotions, creams and gels, for a period of 72 hours prior to study commencement and to use only the assigned test material throughout the study period. The inner forearm region, midway between the wrist and the elbow, was designated as the test area for moisture retention measurements. Test sites of 4 cm×4 cm were delineated using a gentian violet surgical skin marker and standard template. Test materials were applied to the surface of each subject's forearm by a trained technician at a concentration of 2.0 mg/cm2. A baseline NOVA meter measurement of each subject was established by taking readings. In the first test of the study, NOVA meter measurements were taken of each untreated subject at 5 minutes, 15 minutes, 30 minutes, 1 hour and 6 hours. In the second test of the study, the baseline measurement was again established for the same subjects, then a hydrating water mist (L-3001) and a deep moisturizing lotion (L-3004) were applied in succession to each subject's face. Measurements were again taken at 5 minutes, 15 minutes, 30 minutes, 1 hour and 6 hours after application. In the third test of the study, the baseline measurement was again established for the same subjects, then a rainwater-containing hydrating water mist (L-3002) and a rainwater-containing deep moisturizing lotion (L-3003) were applied in succession to each subject's face. Measurements were taken at the same intervals as the first and second tests. The raw data are contained in Table 4, and the results are graphically represented in FIG. 1. The results show that the formulations comprising rainwater provided more rapid moisturization within the first hour and a higher level of moisturization over a 6-hour period. The improvement over the baseline (% Diff) using the formulation comprising pure rainwater (Table 4(c)) is higher than that of the formulation comprising purified water (Table 4(b)). The formulation of the present invention provided an unexpectedly higher degree of sustained moisturization at the end of the 6-hour period of 13% more than when the subject used the formulation using regular purified water. Clearly, the use of pure rainwater with very small, less than trace amounts of minerals and other elements, showed improved moisturization and moisture retention in the test subjects.

TABLE 4

Moisturization Study Results

TABLE 4(a)

| Subject No. | Baseline | 5 min | 15 min | 30 min | 1 h | 6 h |
| --- | --- | --- | --- | --- | --- | --- |
| 60 6747 | 110.67 | 109.33 | 111.33 | 112.00 | 112.00 | 114.67 |
| 48 5321 | 114.00 | 111.33 | 114.67 | 112.67 | 111.33 | 112.00 |
| 64 7285 | 108.00 | 106.00 | 110.00 | 108.00 | 107.33 | 109.33 |
| 74 0758 | 109.33 | 112.00 | 109.33 | 110.67 | 104.67 | 106.00 |
| 56 5529 | 106.67 | 105.33 | 108.00 | 105.33 | 104.67 | 106.00 |
| Mean | 109.73 | 108.80 | 110.67 | 109.73 | 108.80 | 110.27 |
| % Diff | | 0.85% | 0.85% | 0.00% | 0.85% | 0.48% |

Untreated

TABLE 4(b)

Hydrating Water Mist (L-3001) and Deep Moisturizing Lotion (L-3004) (purified water)

| Subject No. | Baseline | 5 min | 15 min | 30 min | 1 h | 6 h |
| --- | --- | --- | --- | --- | --- | --- |
| 60 6747 | 108.00 | 258.00 | 259.33 | 264.00 | 256.67 | 174.00 |
| 48 5321 | 96.00 | 249.33 | 212.00 | 200.00 | 210.67 | 184.00 |
| 64 7285 | 101.33 | 171.33 | 156.67 | 154.33 | 186.67 | 126.00 |
| 74 0758 | 102.00 | 177.33 | 170.67 | 191.33 | 153.33 | 129.33 |
| 56 5529 | 102.67 | 227.33 | 224.00 | 246.00 | 216.67 | 247.33 |
| Mean | 102.00 | 216.66 | 204.53 | 211.13 | 204.80 | 172.13 |
| % Diff | | 112.42% | 100.52% | 106.99% | 100.79% | 68.76% |

TABLE 4(c)

Hydrating Water Mist (L-3002) and Deep Moisturizing Lotion (L-3003) (pure rainwater)

| Subject No. | Baseline | 5 min | 15 min | 30 min | 1 h | 6 h |
| --- | --- | --- | --- | --- | --- | --- |
| 60 6747 | 105.33 | 297.33 | 255.33 | 286.00 | 277.33 | 204.67 |
| 48 5321 | 93.33 | 198.33 | 183.33 | 173.33 | 176.00 | 154.00 |
| 64 7285 | 104.00 | 202.67 | 183.33 | 174.00 | 212.67 | 141.33 |
| 74 0758 | 107.33 | 192.00 | 204.67 | 193.33 | 162.00 | 140.67 |
| 56 5529 | 108.00 | 253.33 | 290.67 | 246.00 | 239.33 | 300.67 |
| Mean | 103.60 | 228.73 | 223.47 | 214.53 | 213.47 | 188.27 |
| % Diff | | 120.79% | 115.70% | 107.08% | 106.05% | 81.73% |

The foregoing examples are not intended to limit the scope of the present invention, which is set forth in the following claims. In particular, various equivalents and substitutions will be recognized by those skilled in the art in view of the foregoing disclosure, and these are contemplated to be within the scope of the invention.

The invention claimed is:

1. A method of increasing moisture absorption in human skin in need thereof comprising the following steps:
  a. applying to the skin an effective amount of a hydrating mist comprising pure Pacific Ocean rainwater;
  b. allowing hydrating mist to absorb into the skin for about 30 seconds;
  c. applying to the skin an effective amount of a moisturizing lotion comprising pure Pacific Ocean rainwater; and
  d. allowing moisturizing lotion to absorb into the skin for about 30 seconds,
  wherein the hydrating mist and moisturizing lotion each comprise 5-99% by weight of pure Pacific Ocean rainwater, and between 0.1 to 10% by weight of each of the following extracts: resurrection plant extract, passion fruit extract, sea buckthorn extract, orchid extract, pomegranate extract and *portulaca* extract, and wherein the pure Pacific Ocean rainwater is gathered off the Northern Pacific Coastline of the United States and has a practical quantitation limit of 0.50 mg/L for sodium, 10 mg/L for hardness, 1 mg/L for calcium and 1 mg/L for magnesium.

2. The method of claim 1 wherein said hydrating mist comprises between 0.2 to 5% by weight of each extract.

3. The method of claim 1 wherein said moisturizing lotion comprises between 0.2 to 5% by weight of each extract.

4. The method of claim 1 wherein said hydrating mist further comprises 0.1-5% by weight of each of the following: *Hamamelis Virginiana* (Witch Hazel) Water, Alcohol (denatured), Sodium Hyaluronate, naturally-derived Glycerin, *Anastatica Hierochuntica* (Resurrection Plant) Extract, *Hippophae Rhamnoides* (Sea Buckthorn) Extract, *Passiflora Incarnata* Fruit (Passion Fruit) Extract, *Orchis Mascula* (Orchid) Flower Extract, *Punica Granatum* (Pomegranate) Extract, *Portulaca Oleracea* Extract, Methyl Diisopropyl Propionamide, Ethyl Menthane Carboxamide, Menthyl Lactate, Lauryl Laurate, *Zea Mays* (Corn) Starch, Hydrolyzed Corn Starch, Hydrolyzed Corn Starch Octenylsuccinate, and one or more natural preservatives and one or more natural aroma-imparting oils.

5. The method of claim 4 wherein the one or more natural preservatives are *Lonicera Caprifolium* (Honeysuckle) Flower Extract and *Lonicera Japonica* (Honeysuckle) Flower Extract.

6. The method of claim 4 wherein the one or more natural aroma-imparting oils are selected from the group consisting of: Citronellol, Limonene, Linalool, *Citrus Aurantium Dulcis* (Orange) Peel Oil, Aldehyde C-14 Natural, *Cinnamomum Zeylanicum* Leaf Oil, *Illicium Verum* (Anise) Fruit/Seed Oil, Benzyl Acetate Natural, *Cinnamomum Cassia* Oil, *Mentha Arvensis* Leaf Oil, *Pyrus Malus* (Apple) Oil, *Cymbopogon Nardus* (Citronella) Oil, *Cucumis Sativus* (Cucumber) Oil, *Prunus Amygdalus Dulcis* (Sweet Almond) Oil, *Pelargonium Graveolens* Extract, *Corylus Avellana* (Hazel) Seed Oil, *Cymbopogon Martini* Oil, *Cymbopogon Schoenanthus* Oil, *Listea Cubeba* Fruit Oil, *Cinnamomum Camphora* (Camphor) Bark Oil, *Citrus Medica Limonum* (Lemon) Peel Oil, *Mentah Citrata* Leaf Extract, and *Pinus Palustris* Oil.

7. The method of claim 1 wherein said moisturizing lotion further comprises 0.1-5% by weight of each of the following: naturally-derived Glycerin, Dimethicone, Cetearyl Alcohol, Caprylic/Capric Triglyceride, *Butyrospermum Parkii* (Shea Butter), Candelilla/Jojoba/Rice Bran Polyglyceryl-3 Esters, Glyceryl Stearate, *Carthamus Tinctorius* (Safflower) Seed Oil, Cetearyl Glucoside, *Borago Officinalis* Seed Oil, *Oenothera Biennis* (Evening Primrose) Oil, *Anastatica Hierochuntica* Extract, *Hippophae Rhamnoides* Extract, *Passiflora Incarnata* Fruit Extract, *Orchis Mascula* Flower Extract, *Punica Granatum* Extract, Sodium Hyaluronate, Tocopheryl Acetate, Sodium Stearyl Lactylate, Sodium Coco-Glucoside Tartrate, Disodium Coco-Glucoside Tartrate, *Triticum Vulgare* (Wheat Germ) Oil, *Persea Gratissima* (Avocado) Oil, Algae Extract, *Zea Mays* (Corn) Starch, Hydrolyzed Corn Starch, Hydrolyzed Starch Octenylsuccinate, Cocamidopropyl Dimethylamine, Lauryl Laurate, Palmitoyl Tripeptide-5, *Portulaca Oleracea* Extract, and one or more natural preservatives and one or more natural aroma-imparting oils.

8. The method of claim 7 wherein the one or more natural preservatives are *Lonicera* Caprifolium (Honeysuckle) Flower Extract and *Lonicera Japonica* (Honeysuckle) Flower Extract.

9. The method of claim 7 wherein the one or more natural aroma-imparting oils are selected from the group consisting of: Geraniol, Amyl Cinnamal, Cinnamal, Citral, Citronellol, Limonene, Linalool, *Citrus Aurantium Dulcis* (Orange) Peel Oil, Aldehyde C-14 Natural, *Cinnamomum Zeylanicum* Leaf Oil, *Illicium Verum* (Anise) Fruit/Seed Oil, Benzyl Acetate Natural, *Cinnamomum Cassia* Oil, *Mentha Arvensis* Leaf Oil, *Pyrus Malus* (Apple) Oil, *Cymbopogon Nardus* (Citronella) Oil, *Cucumis Sativus* (Cucumber) Oil, *Prunus Amygdalus Dulcis* (Sweet Almond) Oil, *Pelargonium Graveolens* Extract, *Corylus Avellana* (Hazel) Seed Oil, *Cymbopogon Martini* Oil, *Cymbopogon Schoenanthus* Oil, *Listea Cubeba* Fruit Oil, *Cinnamomum Camphora* (Camphor) Bark Oil, *Citrus Medica* Limonum (Lemon) Peel Oil, *Mentha Citrata* Leaf Extract, and *Pinus Palustris* Oil.

* * * * *